(12) United States Patent
Tham

(10) Patent No.: US 8,770,192 B2
(45) Date of Patent: Jul. 8, 2014

(54) SYSTEM AND METHOD OF PREVENTING THE DELIVERY OF HYPOXIC GASES TO A PATIENT

(75) Inventor: Robert Q. Tham, Middleton, WI (US)

(73) Assignee: General Electric Company, Schenectady, NY (US)

(*) Notice: Subject to any disclaimer, the term of this patent is extended or adjusted under 35 U.S.C. 154(b) by 850 days.

(21) Appl. No.: 12/987,544

(22) Filed: Jan. 10, 2011

(65) Prior Publication Data

US 2012/0174926 A1 Jul. 12, 2012

(51) Int. Cl.
| | | |
|---|---|---|
| *A61M 11/00* | (2006.01) |
| *A61M 16/00* | (2006.01) |
| *A61M 16/08* | (2006.01) |
| *A61M 16/12* | (2006.01) |
| *A61M 16/20* | (2006.01) |
| *A61M 16/01* | (2006.01) |
| *A61M 16/18* | (2006.01) |
| *A61M 16/22* | (2006.01) |
| *A61M 16/10* | (2006.01) |

(52) U.S. Cl.
CPC ... *A61M 16/0051* (2013.01); *A61M 2202/0208* (2013.01); *A61M 2202/0291* (2013.01); *A61M 16/18* (2013.01); *A61M 2205/52* (2013.01); *A61M 16/0045* (2013.01); *A61M 2202/0241* (2013.01); *A61M 2205/18* (2013.01); *A61M 2202/0283* (2013.01); *A61M 16/0891* (2013.01); *A61M 16/122* (2013.01); *A61M 16/209* (2013.01); *A61M 2205/50* (2013.01); *A61M 2202/025* (2013.01); *A61M 16/22* (2013.01); *A61M 16/01* (2013.01); *A61M 2016/1025* (2013.01); *A61M 16/125* (2013.01); *A61M 2016/1035* (2013.01); *A61M 16/12* (2013.01)
USPC ............ 128/204.21; 128/205.24; 128/205.13; 128/205.12

(58) Field of Classification Search
USPC ............. 128/204.18, 204.21–204.23, 204.26, 128/204.28, 205.11–205.13, 205.17, 205.24
See application file for complete search history.

(56) References Cited

U.S. PATENT DOCUMENTS

| | | | |
|---|---|---|---|
| 4,266,573 A | | 5/1981 | Braatz |
| 5,806,513 A | * | 9/1998 | Tham et al. .............. 128/204.22 |

(Continued)

FOREIGN PATENT DOCUMENTS

| | | |
|---|---|---|
| EP | 0835672 A2 | 4/1998 |
| EP | 0894506 A2 | 2/1999 |

(Continued)

OTHER PUBLICATIONS

Search Report and Written Opinion from EP Application No. 13174980.6 dated Feb. 25, 2014.

(Continued)

*Primary Examiner* — Steven Douglas
(74) *Attorney, Agent, or Firm* — Andrus Intellectual Property Law, LLP

(57) ABSTRACT

A system for preventing the delivery of hypoxic gases during respiratory support of a patient includes a breathing circuit. An input device is operable by a clinician to input at least one ventilator parameter value. A fresh gas manifold is pneumatically connected to the breathing circuit and the fresh gas manifold is configured to provide at least oxygen and balanced gas to the breathing circuit. A digital signal processor is communicatively connected to the input device and the fresh gas manifold. The digital signal processor receives the input at least one ventilation parameter value, calculate a predicted oxygen concentration, and compares the predicted oxygen concentration to a predetermined minimal oxygen required threshold of the patient. A method of preventing the delivery of hypoxic gases to a patient includes providing ventilatory support to the patient through a breathing circuit. A digital signal processor receives a ventilation parameter value from an input device. The digital signal processor calculates a predicted oxygen concentration, compares the predicted oxygen concentration to a predetermined hypoxic concentration threshold and accepts the ventilation parameter value if the predicted oxygen concentration is above the predetermined hypoxic concentration threshold.

20 Claims, 2 Drawing Sheets

(56) References Cited

U.S. PATENT DOCUMENTS

| | | |
|---|---|---|
| 6,041,777 A | 3/2000 | Faithfull et al. |
| 6,619,289 B1 | 9/2003 | Mashak |
| 6,725,860 B2 | 4/2004 | Wallroth et al. |
| 6,828,910 B2 | 12/2004 | VanRyzin et al. |
| 7,305,988 B2 | 12/2007 | Acker et al. |
| 7,334,578 B2 * | 2/2008 | Biondi et al. ............ 128/204.23 |
| 7,556,036 B2 | 7/2009 | Bouillon et al. |
| 7,762,255 B2 | 7/2010 | Mills |
| 2002/0148471 A1 | 10/2002 | Hirabayashi |
| 2007/0173729 A1 | 7/2007 | Fisher et al. |
| 2007/0181126 A1 | 8/2007 | Tolmie et al. |
| 2008/0029092 A1 | 2/2008 | Heesch |
| 2012/0174926 A1 | 7/2012 | Tham |

FOREIGN PATENT DOCUMENTS

| | | |
|---|---|---|
| EP | 0911052 A2 | 4/1999 |
| EP | 1072279 A1 | 1/2001 |
| EP | 2474334 A1 | 7/2012 |
| WO | 2007033271 A1 | 3/2007 |
| WO | 2010033439 A2 | 3/2010 |

OTHER PUBLICATIONS

Datex-Ohmeda Anesthesia Delivery Unit; User's Reference Manual; Document No. 8501700-2; Mar. 23, 2003.

Search Report and Written Opinion from corresponding EP Application No. 12150356.9, Apr. 26, 2012.

Tsai-Hsin Chen et al. "The Relations Between Oxygen Consumption and the Equilibrated Inspired Oxygen Fraction in an Anesthetic Circle Breathing System: A Mathematic Formulation & Laboratory Simulations", Annals of Biomedical Engineering, vol. 37, No. 1, Jan. 1, 2009, pp. 246-254.

Takafumi Azami et al. "Calculation of 02 Consumption During Low-Flow Anesthesia from Tidal Gas Concentrations, Flowmeter, and Minute Ventilation", Journal of Clinical Monitoring and Computing, Kluwer Academic Publishers, DO, vol. 18, No. 5-6, Dec. 1, 2004, pp. 325-332.

Baum, Jan A., "Low Flow Anaesthesia: The Theory and Practice of Low Flow, Minimal Flow and Closed System Anaesthesia", Published by Butterworth-Heinemann on Apr. 12, 1996 ISBN 0750621273 pp. 40-45.

Anesthesia Worksations Brochure, Draeger Medical, Inc. Copyrighted 2011.

Search Report and Written Opinion from EP Application No. 09820048.8 dated Jan. 9, 2014.

Search Report and Written Opinion from EP Application No. 09820048.8 dated Nov. 7, 2013.

* cited by examiner

SYSTEM AND METHOD OF PREVENTING THE DELIVERY OF HYPOXIC GASES TO A PATIENT

BACKGROUND

The present disclosure is related to the field of mechanical ventilation. More specifically, the current disclosure is related to the prevention of the delivery of hypoxic gases to a patient.

Known guards against the delivery of hypoxic gases are based upon minimum concentration settings to ensure the addition of adequate fresh gas oxygen to a breathing circuit. Such a minimum concentration setting is maintained with a mechanical or equivalent link between the gas flow settings of the constituent gases of the delivered fresh gas. Such linkages ensure that the resulting mixture of fresh gas maintains a required minimum oxygen concentration.

During some mechanical ventilator operational settings, particularly low flow mechanical ventilator operation, hypoxic gases can still be delivered to a patient, even when known hypoxic guards register that the minimum oxygen concentration for fresh gas flows has been met.

SUMMARY

A system for preventing the delivery of hypoxic gases during respiratory support of a patient includes a breathing circuit. A fresh gas manifold is pneumatically connected to the breathing circuit. A mechanical ventilator is pneumatically connected to the breathing circuit. A digital signal processor is communicatively connected to an input device, the fresh gas manifold, and the mechanical ventilator. The digital signal processor receives at least one ventilation parameter value, calculates a predicted oxygen concentration delivered to the patient, and compares the predicted oxygen concentration to a predetermined minimum oxygen requirement threshold of the patient. The digital signal processor accepts the at least one ventilation parameter value if the predicted oxygen concentration is above the threshold. The digital signal processor rejects the at least one ventilation parameter value if the oxygen concentration is below the predetermined minimum oxygen requirement threshold.

A low-flow ventilation system that provides repeating breaths of respiratory support to a patient while preventing the delivery of hypoxic gases to the patient includes a breathing circuit with a patient connection configured to deliver the respiratory support to the patient. An input device is operable by a clinician to input at least one ventilation parameter value. A fresh gas manifold is pneumatically connected to the breathing circuit. The fresh gas manifold is configured to provide at least oxygen and a balance gas to the breathing circuit. A digital signal processor is communicatively connected to the input device and the fresh gas manifold. The digital signal processor receives the at least one ventilation parameter value, calculates a predicted oxygen concentration delivered to the patient and compares the predicted oxygen concentration to the minimum oxygen threshold of the patient. The digital signal processor accepts the at least one ventilation parameter value if the predicted oxygen concentration is above the minimum oxygen threshold. If the predicted oxygen concentration is below the predetermined minimum oxygen threshold, the digital signal processor calculates a value for at least one additional parameter such that the predicted oxygen concentration is above the predetermined minimum oxygen threshold. The digital signal processor accepts the at least one ventilation parameter value and at least one additional parameter value.

A method of preventing the delivery of hypoxic gases to a patient includes providing ventilatory support to the patient through a breathing circuit pneumatically connected to a mechanical ventilator. A digital signal processor receives a ventilation parameter value from an input device connected to the digital signal processor. The digital signal processor calculates a predicted oxygen concentration delivered to the patient based upon the ventilation parameter value. The digital signal processor compares the predicted oxygen concentration to a predetermined hypoxic concentration threshold. The digital signal processor accepts the ventilation parameter if predicted oxygen concentration is above the predetermined hypoxic concentration threshold. The digital signal processor rejects the ventilation parameter value if the predicted oxygen concentration is below the predetermined hypoxic concentration threshold.

DETAILED DISCLOSURE

Figure 1:
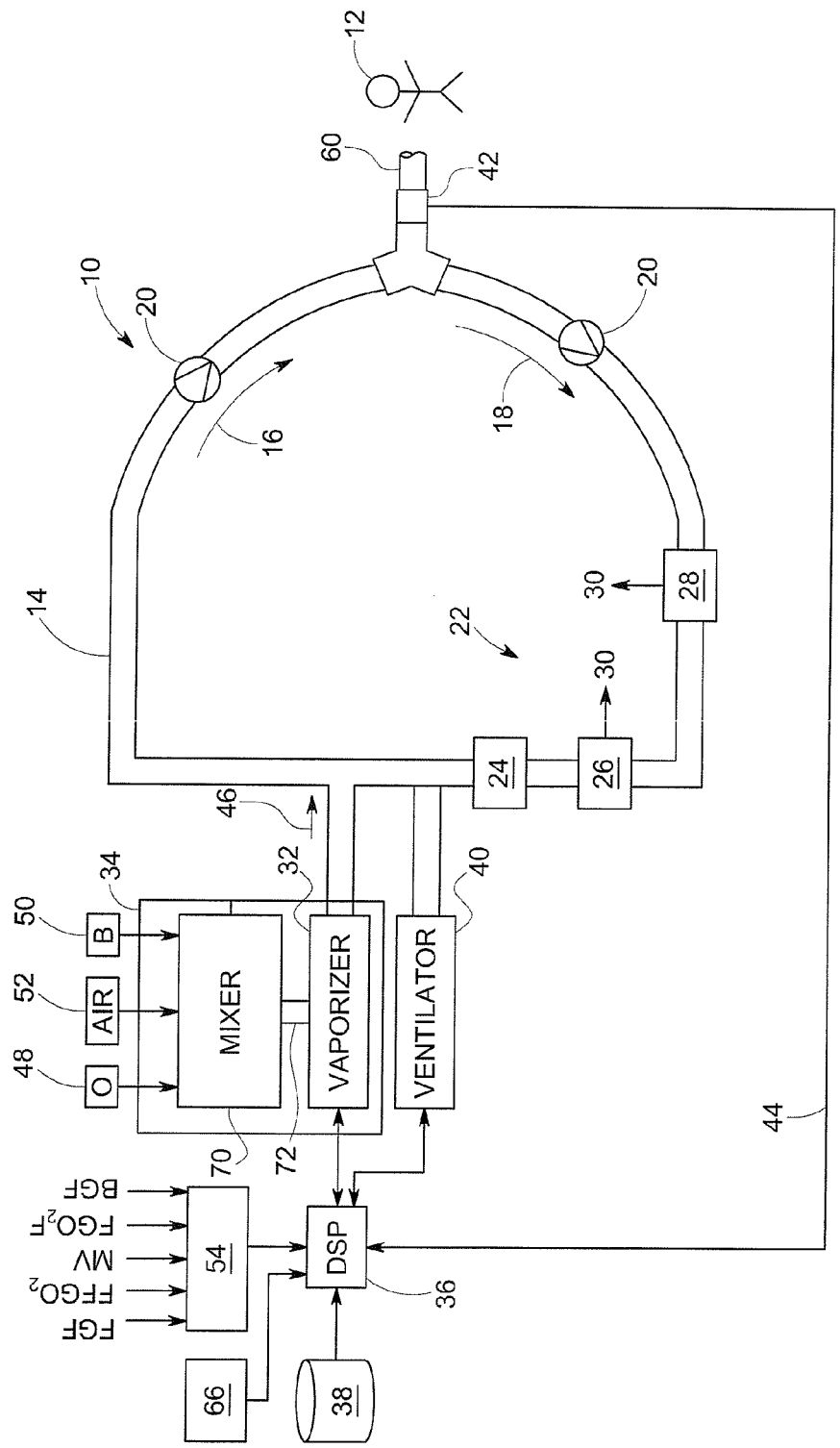
FIG. 1 is a schematic diagram of an embodiment of a low-flow ventilation system.

FIG. 1 is a schematic diagram of a system 10 for providing respiratory support to a patient 12 while preventing the delivery of hypoxic gases to the patient 12.

A respiratory support system 10 includes a breathing circuit 14 through which inspiratory gases 16 are provided to the patient and expired gases 18 are directed from the patient 12. Check valves 20 within the breathing circuit 14 ensure the unidirectional flow of gas within the breathing circuit 14.

In a high flow respiratory support system most or all of the expired gases 18 are vented (not depicted) to the ambient air.

In low flow respiratory support system, gases are added and removed from the breathing circuit 14. Attributed to metabolism, the patient 12 adds carbon dioxide and removes oxygen from the breathing circuit 14. During expiration, the expired gases 18 are directed to an absorber 24 where the carbon dioxide produced by the patient 12 is removed. Some small amount of gas 28 (less than 0.3 liters per min) is leaked from the breathing circuit 14. The remaining expired gas volume is stored in the ventilator 40 to be kept in reserve for the next tidal breath. To make up for the loss of gases by the patient 12 and leaks 28, fresh gas 46 is added to the breathing circuit. Typically the fresh gas 46 is added (about 1 to 3 liters per min) in excess of the total gas loss and forces the removal of some of the expired gas 18 through a relief valve 26. Concentration of gases from the relief valve 26 have approximately the same concentration as the patient expired gases. The ventilator 40 delivers the next tidal breath by compressing the remaining reserve volume. The unidirectional check valves 20 control the direction of gas flow in the breathing circuit 14 for the gases going to and from the patient 12.

In this embodiment, the fresh gas 46 comes from the fresh gas manifold 34. The fresh gas 46 consists of at least of two medical gases from a mixer 70 and/or an anesthetic vapor from an anesthetic vaporizer 32. Fresh gas from the mixer 70 is provided through conduit 72 to the anesthetic vaporizer 32. In the vaporizer 32, a portion of the gas is diverted through a sump (not depicted) of the vaporizer 32 to serve as a carrier gas to pick up an amount of saturated anesthetic vapor according to the concentration settings of the vaporizer 32. All the gases from the mixer 70 and the anesthetic vapor from the vaporizer 32 are pneumatically conducted as fresh gas 46 via conduit 74 to the breathing circuit 14.

In another embodiment, the anesthetic vaporizer 32 directly injects the required anesthetic vapor into the breathing circuit 14 via conduit 74. Since no carrier gas is required to pick up the anesthetic vapor, the gases from mixer 70 is added directly to the breathing circuit 14 by rerouting the outlet of conduit 72 from the anesthetic vaporizer 32 to the breathing circuit 14 (not shown). Conceptually the replacement fresh gas 46 from the fresh gas manifold 34 consists all of the gases and vapor in the conduits 72 and 74.

A normal range of oxygen concentration inspired by the patient 12 is between 21% and 30%. A normal range of an oxygen concentration in gases expired by the patient 12 is between 17% and 25%.

Therefore, under normal conditions, the expired breathing gases may contain an oxygen concentration of 17% which is only 80% of the minimum required oxygen concentration (21%) to be recirculated to the patient. In high fresh gas flow respiratory support systems, this is not a problem as the fresh gas is held at a minimum oxygen concentration of 21% with current hypoxic guards. However, in a low-flow system, even though the gas loss 26, 28 in the respiratory support system is small and this requires only a small amount of replacement fresh gas, the effect of this gas loss on the required composition of the fresh gas is significant. Under these conditions, even though the minimum gas concentration level (e.g. 21%) at the fresh gas manifold 34 is met, the small volume of fresh gas is insufficient to raise the oxygen concentration of the inspired gases 16 delivered to the patient to the minimum oxygen concentration (e.g. 21%) required by the patient.

Additionally, the patient 12 may require a greater concentration of oxygen due to the physiological condition of the patient 12. In these instances, while the patient 12 may be delivered a technically non-hypoxic gas mixture for the normal population, the inspired gases delivered to the patient 12 may be effectively hypoxic for the oxygen concentration requirements of that specific patient 12.

Therefore, the presently disclosed systems and methods control the provision of fresh gas through the fresh gas manifold 34 in order to prevent the delivery of hypoxic gases to the patient 12.

A digital signal processor (DSP) 36 is communicatively connected to the fresh gas manifold 34 and to the anesthetic vaporizer 32, if one is used. The DSP 36 is further communicatively connected to a computer readable medium 38 that is programmed with computer readable code that upon execution by the DSP 36 causes the DSP 36 to operate in the manner described herein and perform the functions as described herein. The computer readable medium 38 may be any of a variety of configurations of non-volatile memory. In one embodiment, the computer readable medium 38 is an integral part of the DSP 36. In an alternative embodiment, the computer readable medium is a separate component that is communicatively connected to the DSP 36. In one non-limiting embodiment, the computer readable medium 38 is flash memory.

The DSP 36 is connected to a mechanical ventilator 40. The mechanical ventilator 40 is operated by the DSP 36 in order to provide repeating waveforms or breaths of inspired gas 16 to the patient 12. The mechanical ventilator 40 is operated by the DSP 36 to provide a variety of forms of respiratory support, including full ventilation or spontaneous breathing assistance.

A respiratory gas monitor 42 is disposed in or near conduit 60 that is the common y-piece of the breathing circuit 14. The respiratory gas monitor 42 analyzes at least the concentration of the inspired gases 16 flowing into the patient 12 and the expired gases 18 flowing away from the patient 12. The respiratory gas monitor 42 provides a signal 44 that is indicative of the gas concentrations, particularly the oxygen concentration. The respiratory gas monitor 42 further includes a flow sensor such that the DSP 36 is provided with an indication of the flow of gas to and from the patient 12. The DSP 36 receives the measurements of concentration and flow of gas breathed by the patient 12 and uses this information in determining the amount of fresh gas 46 to be introduced to the breathing circuit 14 from the fresh gas manifold 34.

In an alternative embodiment, gas monitors supplemental to, or in replace of, the respiratory gas monitor 42 are used within the breathing circuit 14. Non limiting examples of such gas monitors include an inspiratory gas monitor (not depicted) disposed within the inspiratory limb, or an expiratory gas monitor (not depicted) disposed within the expiratory limb. In addition to these exemplary sensor configurations, alternative suitable configurations would be recognized by a person of ordinary skill in the art.

The fresh gas manifold 34 is connected to one or more sources of medical gas, such as oxygen, nitrous oxide, medical air, heliox, xenon, helium. In practice, the fresh gas manifold 34 is at least connected to an oxygen source 48 and a balance gas source 50. In an alternative embodiment, the fresh gas manifold 34 is connected to an air source. As atmospheric air approximately comprises 21% oxygen and 78% nitrogen, this is a common source of medical gas used with a fresh gas manifold 34 as the concentration of oxygen in the atmospheric air generally meets the minimum hypoxic guard concentrations as discussed above.

An example will highlight differences between previous systems and the systems and methods as disclosed herein. If a normal minute volume of respiratory support to a patient 12 is five liters per minute, then at a minimum oxygen concentration of 21%, the minute volume of oxygen provided to the patient is 1.05 liters per minute. If the gas expired by the patient with metabolic oxygen consumption of 0.2 liters per minute has an oxygen concentration of 17% and 1 liter of gas is lost through the recirculation of the expired gases, then a 17% concentration of oxygen of the 4 liters per minute of recirculated gases will contribute 0.68 liters per minute to the rebreathed inspired gases. Therefore, if 1 liter of fresh gas at 25% oxygen concentration is provided by the fresh gas manifold 34 to replace the lost volume of breathing gases, the minute volume of oxygen in the combined fresh gas and recirculated gas provided as inspiratory gases 16 will only be 0.93 liters per minute or 18.6% oxygen concentration which would be considered a hypoxic mixture and is insufficient to replenish the inspired gas concentration that started at 21%. This shows how the known hypoxic guards at a minimum concentration of 25% can allow hypoxic gas concentrations of less than 21% oxygen to be delivered to the patient.

Rather, in the system 10 disclosed herein, the DSP 36 operates the fresh gas manifold 34 in a manner such as to control the concentration and flow of the fresh gas 46 provided to the breathing circuit 14, based upon the metabolic needs of the patient 12.

The DSP 36 uses a variety of equations in calculating the characteristics of the fresh gas 46 provided to the breathing circuit 14. Equation (1) generally describes the relationship between the fresh gas 46 delivered from the fresh gas manifold 34 and the oxygen concentration requirements of the patient 12 and can be derived based on the conservation of mass at a steady temperature and pressure.

$$FGO_2F = \dot{V}O_2 + FeO_2(FGF - \dot{V}O_2) \quad (1)$$

In the above equation, $FGO_2F$ is the flow rate of fresh gas that is oxygen. $\dot{V}O_2$ is the oxygen uptake rate of the patient. $FeO_2$ is the fractional expired oxygen, which is otherwise known as the concentration of oxygen in the expired gases 18. FGF is the fresh gas flow rate, or the flow rate of the fresh gas 46 provided out of the fresh gas manifold 34. This equation assumes that all the CO2 produced by the patient is completely removed by the carbon dioxide absorber 24. A small correction factor using the fraction of the expired carbon dioxide (typically less than 5 or 6%) can be included to correct the second term in equation 1 to account for the carbon dioxide loss through the relief valve 28 instead of preferentially absorbed by the carbon dioxide absorber 24. The exposure of carbon dioxide to the absorber 24 varies with the location of the absorber 24 and the excess gas relief valve 28. It is also known that if the fresh gas 46 is introduced between the inspiratory unidirection valve and the patient (not shown), the gases lost through the relief valve 28 will include inspiratory gases and more oxygen from the fresh gas is required to ensure non-hypoxic gases delivered to the patient While equation (1) is written with respect to the fractional expired oxygen, in consideration of the conservation of oxygen breathed over a patient breath, the fractional expired oxygen ($FeO_2$) is related to fractional inspired oxygen ($FiO_2$) by the following equation:

$$FiO_2 = FeO_2 + \frac{\dot{V}O_2}{MV} \tag{2}$$

In equation (2), $FiO_2$ is the fractional inspired oxygen, or the concentration of oxygen in the inspiratory gases 16 provided to the patient 12. MV is the minute volume of total gases that are provided to the patient 12 by the respiratory support system 10. The minute volume may be set by a clinician by entering the minute volume into an input device 54. The minute volume is provided by the input device 54 to the DSP 36, and the DSP 36 operates the ventilator 40 to provide respiratory support to the patient 12 that achieves the established minute volume. The MV can also be measured using the respiratory gas monitor 42. The respiratory gas monitor 42 communicates with DSP 36 via connection 44.

One or more ventilation parameter values of the system 10 are controlled by the clinician, such as by inputs into the input device 54. The DSP 36 manages these input ventilation parameter values using equation (1) such that the clinician does not unknowingly establish a combination of values that will result in a hypoxic gas mixture being delivered to the patient 12. In an exemplary embodiment, one or more of the fresh gas flow rate (FGF), the fractional fresh gas oxygen ($FFGO_2$), and the fresh gas oxygen flow rate ($FGO_2F$) are ventilation parameter values that can be controlled by the clinician.

Additionally, the patient oxygen uptake rate ($\dot{V}O_2$) can be obtained in several ways. The oxygen uptake can be measured from the patient by comparing the volume of oxygen inspired and expired by the patient over a breath. In particular, the oxygen uptake is the integral of the instantaneous product of the oxygen concentration and gas flow breathed by the patient over a breath. This oxygen concentration and gas flow is measured by the respiratory gas monitor 42. With the availability of these measurements, some respiratory gas monitors perform the oxygen uptake computation. Alternatively, these measurements can be fed via the signal 44 to the DSP 36 to compute the integration. An estimation of the oxygen uptake can be obtained by multiplying the difference between $FiO_2$ and $FeO_2$ by the MV. The respiratory gas monitor 42 measures the $FiO_2$, $FeO_2$ and MV.

In another embodiment, the oxygen uptake rate may be entered by a clinician through the input device 54 as a clinical judgment or estimation based upon patient demographics. In one example, the oxygen uptake rate can be estimated using the patient's weight and the Brody equation. The DSP 36 calculates the oxygen uptake rate from the inspired oxygen concentration and the expired oxygen concentration using equation (2).

In still further embodiments, the oxygen uptake rate can be crudely estimated based upon safe population base values. This can be assumed to be the easiest, but the least accurate as there is a wide range of population need (e.g. 300 milliliters per minute or more for an adult with a fever, or less than 20 milliliters per minute in a neonate). The relationship of the fresh gas oxygen concentration to the fresh gas flow rate and the fresh gas oxygen flow rate are shown below in equations (3) and (4):

$$FFGO_2 = \frac{FGO_2F}{FGF} \tag{3}$$

$$FGF = \frac{FGO_2F}{FFGO_2} \tag{4}$$

Delivery of fresh gas oxygen and a balance gas requires two parameters to control the fresh gas manifold 34. The complementary pairs can be chosen from the concentration of one of the gases and the total fresh gas flow, or the flow of each individual gas. Two commonly used combinations of these complementary setting pairs are $FFGO_2$ and FGF, or $FGO_2F$ and a balance gas flow rate (BGF). In one embodiment of the disclosed hypoxic guard, the $FGO_2F$ or the FGF is derived using equations 1 and 2 using values of $FiO_2$ or $FeO_2$ that correspond to the desired protection for the delivery of the safe non-hypoxic threshold concentration, and the an estimated or assumed oxygen uptake (VO2). A typical safe threshold value for either $FiO_2$ or $FeO_2$ is 25%. It can be seen from equation 1 that the relationships of the variables are independent of the ventilator parameters. As such, $FeO_2$ works well to establish the safe non-hypoxic delivery to the patient. Since $FiO_2$ is conventionally measured to alarm on hypoxic delivery, the safe $FiO_2$ goals are familiar to operating clinicians and technicians, thus, it is useful in embodiments to use the $FiO_2$ as a safe non-hypoxic gas concentration threshold for gases delivered to the patient. Depending upon the combination of inputs being made by the clinician in the input device 54 (e.g. FGF and. $FFGO_2$, or $FGO_2F$ and BGF) the DSP 36 calculates the threshold value of the parameter being set using the current value of the complementary parameter. The safe input threshold values are the minimum oxygen concentration, the minimum oxygen flow, the minimum fresh gas flow rate, or the maximum balance gas flow rate.

Therefore, if the clinician attempts to enter a value for the fresh gas flow rate (FGF), then the DSP 36 calculates the minimum fresh gas flow rate using equations 1 and 2 using safe non-hypoxic $FiO_2$ or $FeO_2$ threshold concentration, patient oxygen uptake (VO2), and the current set value for the fresh gas oxygen concentration ($FFGO_2$). If the value of the fresh gas flow rate being set is higher than the minimum fresh gas flow rate, the DSP 36 will accept the setting being made, thus ensuring that the gas manifold 34 will be controlled to provide adequate oxygen to the patient 12. If the clinician attempts to input a value for the fresh gas oxygen concentration (FFGO$_2$), the DSP 36 calculates a minimum fresh gas oxygen concentration (FFGO$_2$) using equations 1 and 2 using safe non-hypoxic FiO$_2$ or FeO$_2$ threshold concentration, patient oxygen uptake (VO2), and the current set value for the fresh gas flow rate that must be provided by the fresh gas manifold 34 to provide adequate oxygen in the inspired gases 16 to the patient 12. Settings above the minimum fresh gas oxygen concentration are values that the DSP 36 will accept as safe non-hypoxic values to control the fresh gas manifold 34. As a minimum provision, the clinician should be alerted to a hypoxic setting is attempted.

The relationship between fresh gas flow rate (FGF), balance gas flow rate (BGF), and fresh gas oxygen flow rate (FGO$_2$F) can be determined by the following equation:

$$FGF=BGF+FGO_2F \quad (5)$$

Additionally, combining equation (5) with equations (1) through (4), DSP 36 can calculate the safe non-hypoxic range of FGO$_2$F and BGF settings to control the gas manifold 34. In this complementary pair of fresh gas manifold settings, if the clinician attempts to input a setting value for the BGF, the DSP 36 calculates, using equations 1 through 5, values of safe non-hypoxic FiO$_2$ or FeO$_2$ threshold concentration, patient oxygen uptake (VO2), and the current set value for the FGO$_2$F, a maximum BGF that must not be exceeded to ensure that the fresh gas manifold 34 will be controlled to provide adequate oxygen to the patient 12. Only values that are below the maximum BGF will be accepted by the DSP 36 to control the delivery of gases from the fresh gas manifold 34. Settings above the minimum fresh gas oxygen concentration are values that the DSP 36 will accept as safe non-hypoxic values to control the fresh gas manifold 34. In one embodiment, the clinician is alerted when a hypoxic BGF setting is attempted. In a further embodiment, the DSP 34 uses a similar process when the clinician attempts to set the FGO$_2$F to ensure that only safe non-hypoxic FGO$_2$F settings above the minimum FGO$_2$F is being set or (as a minimum requirement) alert the clinician of a hypoxic FGO$_2$F setting is attempted.

While the above examples have been for single pairs of fresh gas manifold parameters, it is to be recognized that in alternative embodiments, the clinician may input or otherwise establish a plurality of fresh gas manifold parameters. In this case, the DSP 36 would calculate the required minimum or maximum values for the additional parameters with respect to the input values at the equations as described above. The addition of anesthetic vapor into the fresh gas line 46 by the anesthetic vaporizer 32 can be similarly treated as an additional parameter.

In a still further embodiment of the respiratory support system 10, a graphical display 66 is communicatively connected to the DSP 36. The graphical display 66 is operated by the DSP 36 in order to present information regarding the operation and settings of the respiratory support system 10. In an embodiment, when the clinician enters a ventilator parameter value into the input device 54, the DSP 36 determines if the modified ventilator parameter value will result in the delivery of a hypoxic gas mixture to the patient if the remaining fresh gas manifold or ventilator parameter settings remain unchanged. The determination is made by comparing a predicted delivered oxygen gas concentration to a minimal patient oxygen requirement threshold. If the DSP 36 determines that such a change to the ventilator parameter would result in a hypoxic gas mixture delivered to the patient, then the DSP 36 can reject the clinician's entry and produce an alarm, including a visual or audible alarm with the graphical display 66. In an embodiment, the graphical display 66 further presents a prompt or option to the clinician in order to override the alarm, such that the clinician may selectively and deliberately change the ventilator parameter value, despite the warning that such a change on its own will result in the delivery of a hypoxic gas to the patient.

Figure 2:
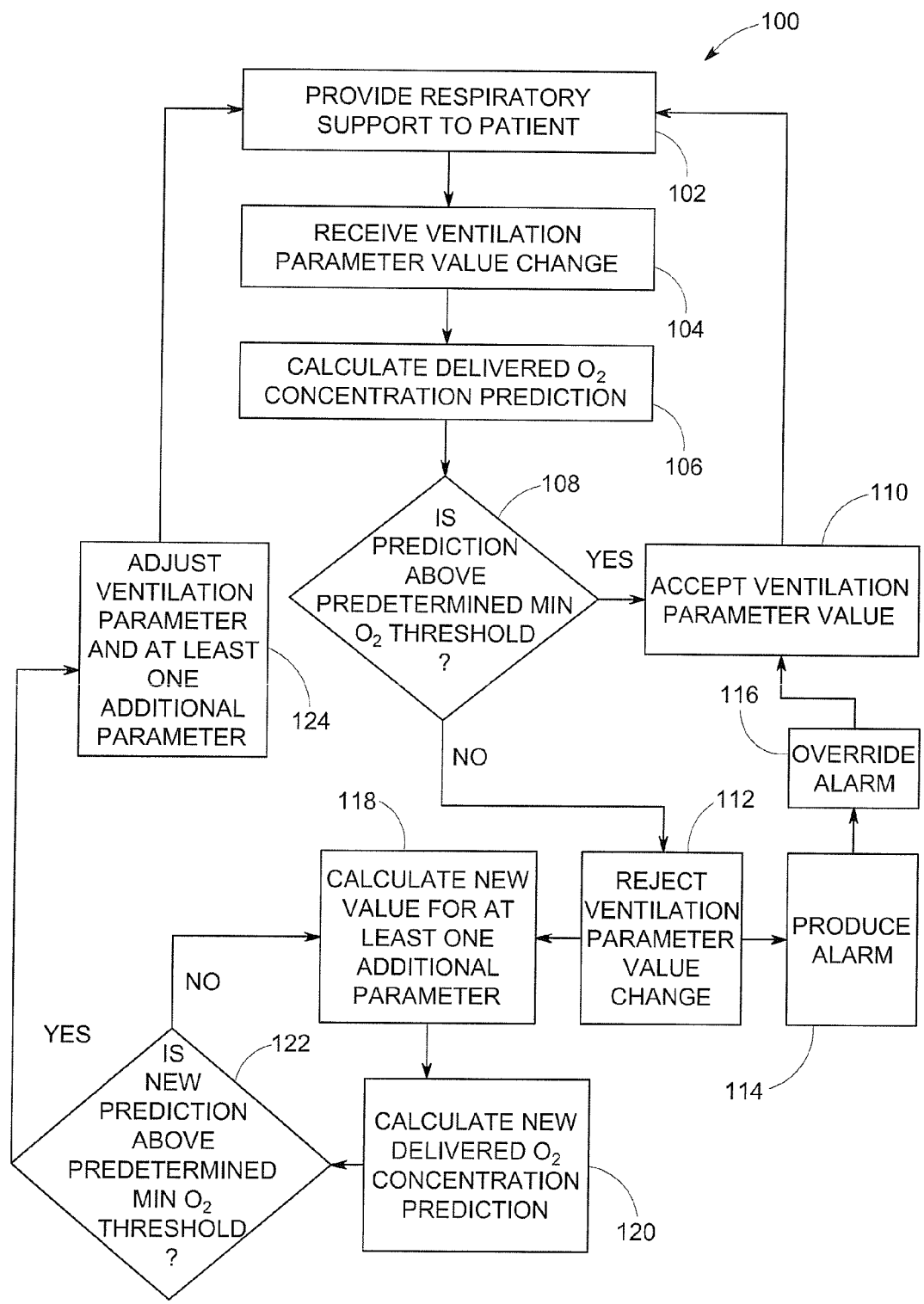
FIG. 2 is a flow chart that depicts an embodiment of a method of preventing the delivery of hypoxic gases to a patient.

FIG. 2 is a flow chart that depicts an embodiment of a method of preventing the delivery of hypoxic gases to a patient. It is to be understood that embodiments of the method as disclosed herein with respect to FIG. 2 need not require each of the steps as detailed herein, nor specifically in the order described herein. Additionally, embodiments of the method may be performed solely through the use of a computer that executes computer readable code stored on a computer readable medium. The technical effect of such embodiments would be to prevent the delivery of hypoxic gases to a patient. Other embodiments of the method may be performed with a respiratory support system such as, but not limited to that depicted and disclosed in FIG. 1.

The method 100 starts with respiratory support being provided to the patient at 102. The respiratory support provided at 102 can either be full mechanical ventilation or can be spontaneous breathing assistance. Additionally, the respiratory support may include the delivery of anesthetic agent or other gaseous or nebulized drugs entrained in the medical gas delivered to the patient.

At 104, a ventilation parameter change is received by a digital signal processor (DSP). In one embodiment, the ventilation parameter value change is received by a clinician entering a change in the ventilation parameter value through an input device. In an alternative embodiment, the ventilation parameter value change is received from an automated fresh gas manifold control system, or as part of a plurality of ventilation parameter value changes. In embodiments, the ventilation parameter value changed by the clinician includes, but is not limited to, FGF, FFGO$_2$, MV, BGO$_2$F, and BGF. A person of ordinary skill in the art would recognize alternative ventilation parameter values that may additionally or alternatively be used in embodiments of the systems and methods as disclosed herein.

The DSP digital signal processor calculates a prediction of the oxygen concentration that will be delivered to the patient at 106 if the ventilation parameter value change is made. As described above with respect to FIG. 1, the calculated delivered oxygen concentration prediction can be calculated using one or more equations as disclosed above that relate the concentration and flow rate of expired gases from the patient and the fresh gas supply to the concentration and flow rate of inspiratory gases provided to the patient.

At 108, the predicted oxygen concentration is compared to a predetermined threshold that is representative of a minimal oxygen metabolic need of the patient. The patient's metabolic oxygen need, or oxygen uptake can be supplied to the digital signal processor in a variety of ways. In some embodiments, the patient oxygen uptake is measured directly or calculated from inspired gas and expired gas oxygen concentration values. Alternatively, a population or other demographic estimate of oxygen need can be used as a substitute for a measured or derived value that would be more patient specific.

If the predicted delivered oxygen concentration is above the predetermined minimum of oxygen concentration threshold, then at 110, the digital signal processor accepts the ventilation parameter value to the value that had been received at 104. The method 100 continues back to 102 where respiratory support is provided to the patient with the new and updated ventilation parameter value.

If the predicted delivered oxygen concentration does not meet the predetermined minimum oxygen concentration threshold, then at 112, the digital signal processor rejects the ventilation parameter value change that was received at 104.

In one embodiment, after the ventilation parameter value change has been rejected at 112, the digital signal processor operates a graphical display or other output device to produce an alarm at 114. The alarm produced at 114 serves to notify the clinician that a hypoxic gas mixture would be delivered to the patient if the ventilation parameter value from 104 were accepted. The alarm may further include a prompt for the clinician to override the alarm. At 116, a signal to override the alarm is received. A clinician may enter such an override signal through an input device. This feature or control may be desired by a clinician in an event wherein the clinician has particular knowledge of the specific respiratory therapy or condition of the patient. Therefore, the clinician specific knowledge can be implemented and the clinician can override the alarm to deliver the respiratory support according to the ventilation parameter value input by the clinician. After the alarm is overridden at 116, the ventilation parameter is accepted at 110 and respiratory support is provided to the patient according to the new ventilation parameter value.

Alternatively, after the digital signal processor rejects the ventilation parameter change at 112, the DSP calculates a new value for at least one additional parameter at 118. The DSP calculates at least one additional parameter value change that would be required to accept the input ventilation parameter value change and still prevent the delivery of a hypoxic gas mixture to the patient. In one embodiment, this is performed through an iterative process wherein a new value for at least one additional parameter is used to calculate a new delivered oxygen concentration prediction at 102. The new delivered oxygen concentration prediction is compared to the predetermined threshold at 122. If the new delivered oxygen concentration prediction is still below the threshold, then a new value for the at least one additional parameter is calculated at 118 and the loop repeats. Non-limiting examples of additional parameter values that are changed include the fresh gas oxygen concentration ($FFGO_2$) and the fresh gas flow rate (FGF).

If the new delivered oxygen concentration prediction based upon the received ventilation parameter value and the at least one additional parameter value is above the predetermined threshold at 122, than at 124 the DSP accepts the ventilation parameter value and the at least one additional parameter value. Respiratory support is then provided to the patient using the new ventilation parameter value and at least one additional parameter value.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A system for preventing the delivery of hypoxic gases during respiratory support of a patient, the system comprising:
    a breathing circuit including a patient connection configured to deliver respiratory support to the patient;
    an input device operable by a clinician to input at least one ventilation parameter value;
    a fresh gas manifold pneumatically connected to the breathing circuit, the fresh gas manifold configured to provide at least oxygen and a balance gas to the breathing circuit;
    a mechanical ventilator pneumatically connected to the breathing circuit, the mechanical ventilator configured to create fluid pressure waveforms within the breathing circuit to provide respiratory support to the patient;
    a digital signal processor communicatively connected to the input device, fresh gas manifold, and the mechanical ventilator, the digital signal processor receives the input at least one ventilation parameter value, calculates a predicted oxygen concentration delivered to the patient with the at least one ventilation parameter value, and compares the predicted oxygen concentration to a predetermined minimum oxygen requirement threshold of the patient;
    wherein if the predicted oxygen concentration is above the predetermined minimum oxygen requirement threshold, the digital signal processor accepts the at least one ventilation parameter value; and
    wherein if the predicted oxygen concentration is below the predetermined minimum oxygen requirement threshold, the digital signal processor rejects the at least one ventilation parameter value.

2. The system of claim 1, further comprising an output device, wherein if the digital signal processor rejects the at least one ventilation parameter value, the digital signal processor operates the output device to produce an alarm.

3. The system of claim 2, wherein a clinician can override the alarm with an input to the input device, and the digital signal processor accepts the at least one ventilator parameter value.

4. The system of claim 1, wherein if the digital signal processor rejects the at least one ventilation parameter value, the digital signal processor calculates at least one additional parameter value.

5. The system of claim 4, wherein the digital signal processor recalculates a new predicted oxygen concentration, and if the new predicted oxygen concentration is above the predetermined minimum oxygen requirement threshold, the digital signal processor accepts the at least one ventilation parameter value and at least one additional parameter value.

6. The system of claim 5, wherein the at least one ventilation parameter value comprises fresh gas flow rate and the at least one additional parameter value comprises fresh gas oxygen concentration.

7. The system of claim 5, wherein the at least one ventilation parameter value comprises fresh gas oxygen flow rate and the at least one additional parameter value comprises balance gas flow rate.

8. The system of claim 1, further comprising:
    a respiratory gas monitor fluidly connected to the breathing circuit, the respiratory gas monitor produces a signal indicative of an oxygen concentration inhaled and exhaled by the patient.

9. The system of claim 8, wherein the digital signal processor calculates the predetermined minimum oxygen requirement threshold using at least one of the signal indicative of oxygen concentration inhaled and exhaled by the patient.

10. The system of claim 1, wherein the fresh gas manifold is connected to a nitrous oxide source and the nitrous oxide source provides the balance gas to the breathing circuit.

11. A low-flow ventilation system that provides repeating breaths of respiratory support to a patient while preventing the delivery of hypoxic gases to the patient, the system comprising:
a breathing circuit including a patient connection configured to deliver the respiratory support to the patient;
an input device operable by a clinician to input at least one ventilation parameter value;
a fresh gas manifold pneumatically connected to the breathing circuit, the fresh gas manifold configured to provide at least oxygen and a balance gas to the breathing circuit;
a digital signal processor communicatively connected to the input device and the fresh gas manifold, the digital signal processor receives the at least one ventilation parameter value, calculates a predicted oxygen concentration delivered to the patient with the at least one ventilation parameter value, and compares the predicted oxygen concentration to a predetermined minimum oxygen requirement threshold of the patient;
wherein if the predicted oxygen concentration is above the predetermined minimum oxygen requirement threshold, the digital signal processor accepts the at least one ventilation parameter value; and
wherein if the predicted oxygen concentration is below the predetermined minimum oxygen requirement threshold, the digital signal processor calculates at least one additional parameter value such that the predicted oxygen concentration is above the predetermined minimum oxygen requirement threshold, and the digital signal processor accepts the at least one ventilation parameter value and at least one additional parameter value.

12. The system of claim 11, wherein the at least one ventilation parameter value is selected from fresh gas flow rate, fresh gas oxygen concentration, fresh gas oxygen flow rate, and balance gas flow rate.

13. The system of claim 11, wherein the digital signal processor calculates the predetermined minimum oxygen requirement.

14. The system of claim 13, wherein the digital signal processor receives a value of patient oxygen uptake rate and calculates the predetermined minimum oxygen requirement from the value of patient oxygen uptake rate.

15. The system of claim 13, further comprising:
a respiratory gas monitor fluidly connected to the breathing circuit, the respiratory gas monitor produces a signal indicative of an oxygen concentration inhaled or exhaled by the patient;
wherein the digital signal processor calculates the predetermined minimum oxygen requirement using at least one of the oxygen concentration inhaled by the patient or the oxygen concentration exhaled by the patient.

16. A method of preventing the delivery of hypoxic gases to a patient receiving ventilatory support from low-flow mechanical ventilator, the method comprising:
providing ventilatory support to the patient through a breathing circuit pneumatically connected to a mechanical ventilator in a low-flow configuration;
receiving, with a digital signal processor, a ventilation parameter value from an input device connected to the digital signal processor;
calculating a predicted oxygen concentration delivered to the patient with the digital signal processor based upon the ventilation parameter value;
comparing the predicted oxygen concentration to a predetermined hypoxic concentration threshold with the digital signal processor;
accepting, with the digital signal processor, the ventilation parameter value if the predicted oxygen concentration is above the predetermined hypoxic concentration threshold;
rejecting, with the digital signal processor, the ventilation parameter value if the predicted oxygen concentration is below the predetermined hypoxic concentration threshold.

17. The method of claim 16, further comprising:
calculating at least one additional parameter value with the digital signal processor, the at least one additional parameter value resulting in the predicted oxygen concentration being above the predetermined hypoxic concentration threshold.

18. The method of claim 16, further comprising operating a graphical display with the digital signal processor to represent an alarm if the digital signal processor rejects the ventilation parameter value.

19. The method of claim 16, further comprising:
receiving a value of patient oxygen uptake with the digital signal processor; and
calculating the predetermined hypoxic concentration threshold from the received value of patient oxygen uptake.

20. The method of claim 19, further comprising:
receiving a value of oxygen concentration with the digital signal processor, the value of oxygen concentration measured by a respiratory gas monitor; and
calculating, with the digital signal processor, the predetermined hypoxic concentration threshold from the value of inspired oxygen concentration and the value of expired oxygen concentration.

* * * * *